United States Patent
Moritz

(10) Patent No.: US 7,299,152 B1
(45) Date of Patent: Nov. 20, 2007

(54) CORRELATING EVENT DATA FOR LARGE GEOGRAPHIC AREA

(75) Inventor: Elan Moritz, Lynn Haven, FL (US)

(73) Assignee: United States of America as represented by the Secretary of the Navy, Washington, DC (US)

( * ) Notice: Subject to any disclaimer, the term of this patent is extended or adjusted under 35 U.S.C. 154(b) by 417 days.

(21) Appl. No.: 10/962,817

(22) Filed: Oct. 4, 2004

(51) Int. Cl.
*G06F 19/00* (2006.01)

(52) U.S. Cl. ............ 702/179; 702/180; 702/187; 340/573.1

(58) Field of Classification Search ............ 702/179, 702/180, 187
See application file for complete search history.

(56) References Cited

U.S. PATENT DOCUMENTS

| | | | |
|---|---|---|---|
| 6,873,261 B2* | 3/2005 | Anthony et al. | 340/574 |
| 2002/0193967 A1* | 12/2002 | Siegel | 702/187 |
| 2003/0093187 A1* | 5/2003 | Walker | 701/1 |
| 2005/0043961 A1* | 2/2005 | Torres et al. | 705/1 |
| 2005/0264412 A1* | 12/2005 | Levesque et al. | 340/517 |
| 2005/0283337 A1* | 12/2005 | Sayal | 702/179 |
| 2006/0026017 A1* | 2/2006 | Walker | 705/1 |
| 2006/0109113 A1 | 5/2006 | Reyes et al. | 340/541 |
| 2006/0152372 A1* | 7/2006 | Stout | 340/573.1 |
| 2006/0187018 A1* | 8/2006 | Maurer et al. | 340/521 |

FOREIGN PATENT DOCUMENTS

| | | |
|---|---|---|
| WO | WO2006034246 A2 | 3/2006 |

\* cited by examiner

*Primary Examiner*—Hal Wachsman
(74) *Attorney, Agent, or Firm*—James T. Shepherd

(57) ABSTRACT

Event data associated with possible terrorist activities occurring at geographically-dispersed locations is monitored and analyzed. Event data collected from the locations is delineated by one or more data classes. Statistical analyses performed on the event data are based on one of a number of unique time periods or blocks. Results of the statistical analyses are used in the performance of a number of correlations in order to identify patterns occurring in the data classes and/or correlations between the data classes.

8 Claims, 2 Drawing Sheets

CORRELATING EVENT DATA FOR LARGE GEOGRAPHIC AREA

ORIGIN OF THE INVENTION

The invention described herein was made in the performance of official duties by an employee of the Department of the Navy and may be manufactured, used, licensed by or for the Government for any governmental purpose without payment of any royalties thereon.

FIELD OF THE INVENTION

The invention relates generally to data correlation, and more particularly to correlating event data associated with activities of concern occurring at a plurality of locations dispersed over a large geographic area.

BACKGROUND OF THE INVENTION

On a local level, defense, security and law enforcement agencies spend a lot of time and effort to protect sensitive sites or those located in hostile regions. Thus, a variety of systems and methods exist and are being developed to improve security at individual sites. However, in recent history, the world has been subjected to multiple coordinated terrorist attacks occurring close in time at multiple locations. Post-event analysis of these attacks has revealed various geographically-dispersed pre-event activities that, when examined in isolation by local security forces, did not appear to be indicative of threatening events. However, when examined collectively, these geographically-dispersed pre-event activities produced patterns in windows of time that clearly represented highly suspicious activity warranting immediate attention.

SUMMARY OF THE INVENTION

Accordingly, it is an object of the present invention to provide a method and system for monitoring and analyzing event data associated with activities of concern occurring at a plurality of locations dispersed over a large geographic area.

Another object of the present invention is to provide a method and system for monitoring and analyzing events occurring at a plurality of geographically-dispersed locations in order to identify patterns or correlations between events.

Other objects and advantages of the present invention will become more obvious hereinafter in the specification and drawings.

In accordance with the present invention, event data associated with activities of concern occurring at a plurality of locations dispersed over a large geographic area is monitored and analyzed. Raw data packages are collected from the locations. Each raw data package includes data that describes at least one of the following data classes:
  (i) date and time of an event,
  (ii) means used to collect the data at that location,
  (iii) a record of the event;
  (iv) type of location where the event occurred,
  (v) identification data collected at the event and associated with individuals involved in the event,
  (vi) a category assigned to the event at that location,
  (vii) an evaluation of the event that originates at that location, and
  (viii) a response to the event implemented at that location.

A plurality of statistical analyses are performed using the raw data packages. Each statistical analysis is based on one of a plurality of unique time periods such that each statistical analysis relates ones of the raw data packages occurring in a most recent one of the unique time periods to ones of the raw data packages occurring in historical ones of the unique time periods. Results of the statistical analyses are stored and used in the performance of a plurality of correlations in order to identify at least one of the following:
  (i) patterns occurring in the data classes,
  (ii) a correlation score that exceeds a predetermined threshold in at least one of the data classes, and
  (iii) occurrence of a particular type of category assigned to the event.

The present invention is particularly useful in identifying coordinated activities at a number of geographically-dispersed locations that may be indicative of terrorist activity.

BRIEF DESCRIPTION OF THE DRAWINGS

Other objects, features and advantages of the present invention will become apparent upon reference to the following description of the preferred embodiments and to the drawing, wherein corresponding reference characters indicate corresponding parts of the drawing and wherein.

DETAILED DESCRIPTION OF THE INVENTION

Figure 1:
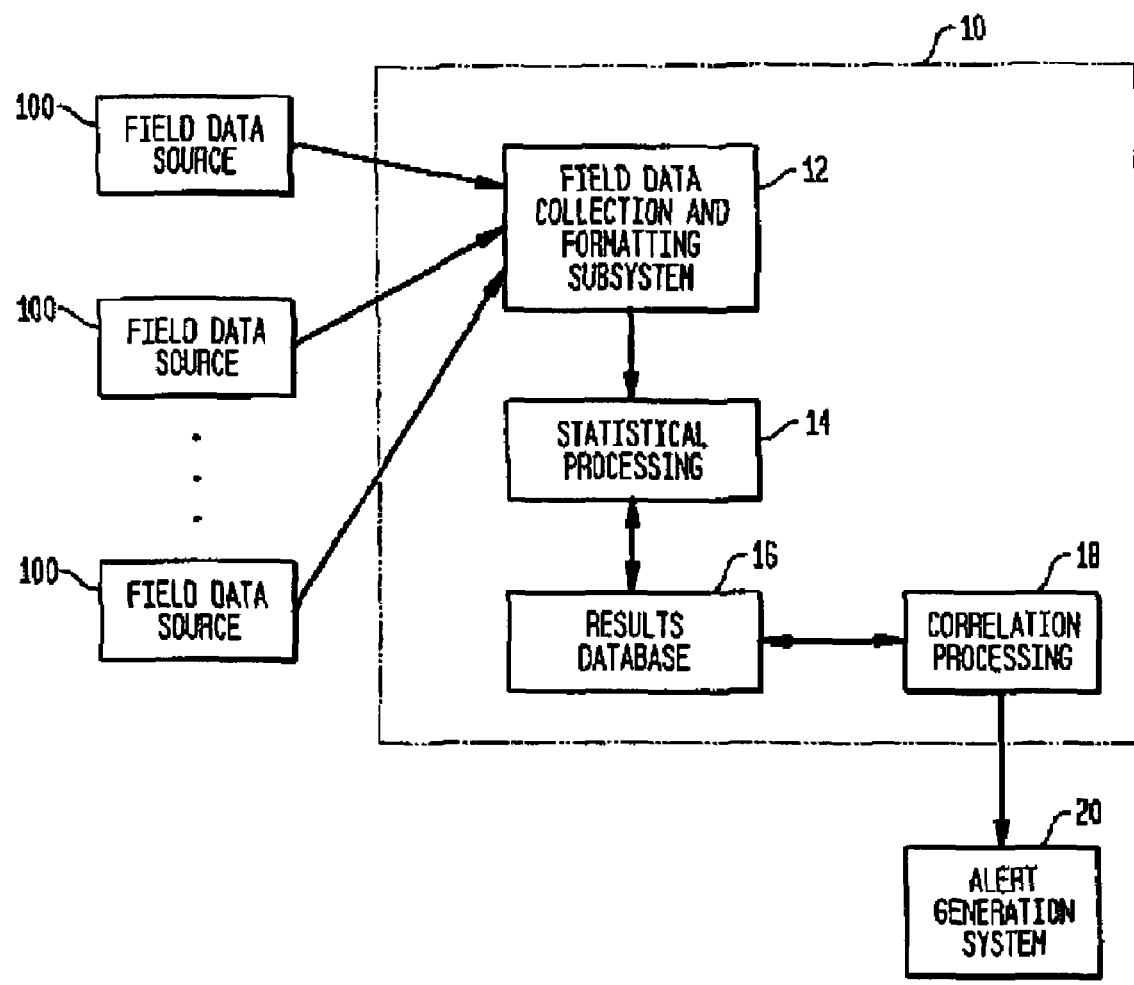
FIG. 1 is a block diagram of a system for monitoring and analyzing event data associated with activities of concern occurring at a plurality of locations dispersed over a large geographic area in accordance with the present invention.
Figure 2:
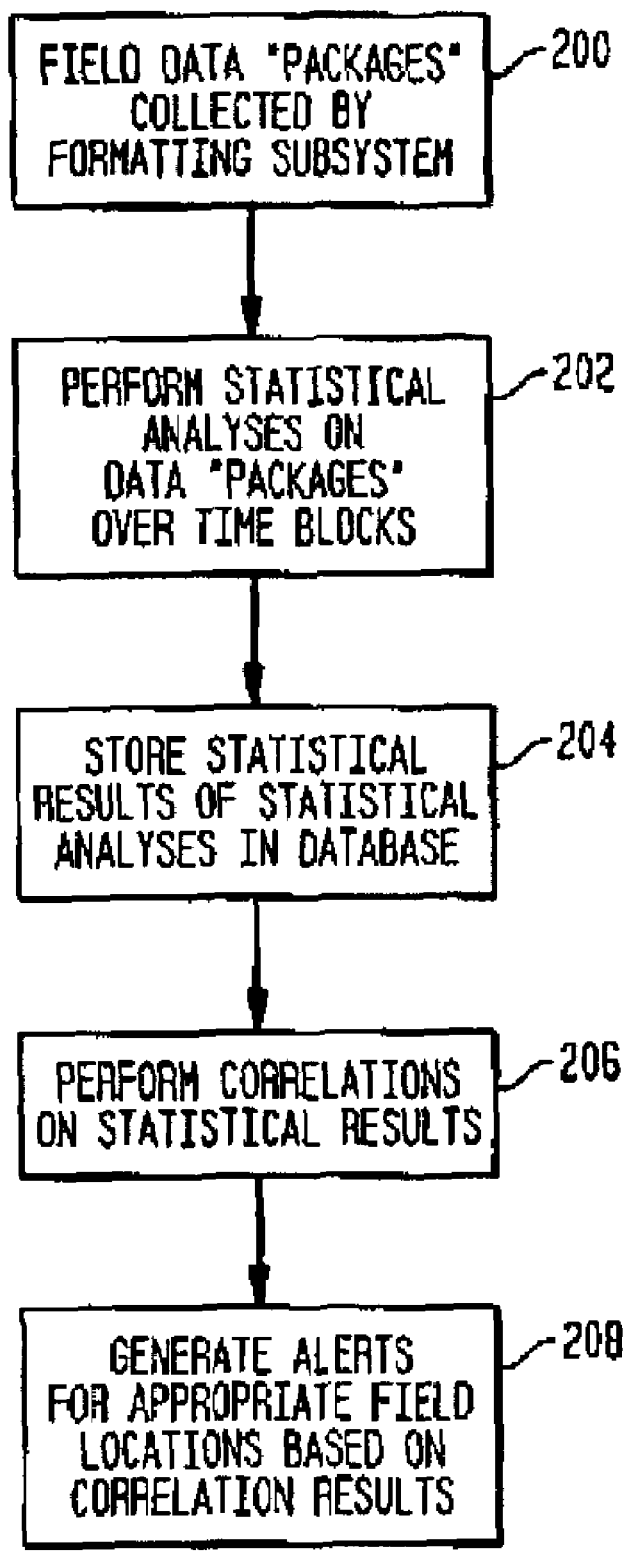
FIG. 2 is a top-level flow diagram of the method of monitoring and analyzing event data associated with activities of concern in accordance with the present invention.

Referring now to the drawings, simultaneous reference will be made to FIGS. 1 and 2 where FIG. 1 is a top-level system diagram and FIG. 2 is a top-level flow diagram in accordance with the present invention. In FIG. 1, a system for monitoring and analyzing geographically-dispersed event data in accordance with the present invention is shown within the dashed line box referenced by numeral 10. As used herein, the term "geographically-dispersed" refers to geographic locations dispersed (i.e., separated by distances of hundreds or thousands of yards up to tens, hundreds or thousands of miles) over large geographic areas such as a country, a continent, or multiple continents. The term "location" is used herein to refer to any government installation or building, or any civilian installation or building. Examples of such locations include, but are not limited to, military compounds, government buildings, embassies, airports, financial centers, mass transportation facilities, ports, border crossings, sports arenas, oil/gas refineries, utility plants, etc.

It is assumed herein that system 10 is located at a secure facility and that each location coupled to system 10 has its own field data source 100 associated therewith. Each field data source 100 will typically have principle system components that can include sensors, communication nodes and communication pathways, processing nodes, data storage/archive nodes, reaction sub-systems, and methods, processes, and procedures for evaluating data and information by combined human and machine (i.e., computer) teams or by machines alone. For example, each field data source 100 can be equipped with a variety of objective event recording systems (e.g., video and/or image recording systems, audio recording systems, etc.). One or more of field data sources 100 could also be equipped with systems that objectively identify individuals involved in an event. The identity of an individual or vehicle could be stored on a individual/vehicle-carried identification tag that is read by a system as the individual/vehicle enters a site as disclosed in detail in pending U.S. patent application Ser. No. 10/923,254, filed Aug. 16, 2004, the contents of which are hereby incorporated by reference.

Identity information can further include biometric data collected on-site by a system such as that disclosed in pending U.S. patent application Ser. No. 10/914,779, filed Aug. 6, 2004, the contents of which are hereby incorporated by reference.

Other types of objective data originating from each field data source 100 could include the date and time of each event, the type of systems/methods used to collect the data associated with the event (i.e., to serve as an indicator of data integrity), and the type of location where the event occurred (e.g., airport, embassy, border crossing, port, etc.). In addition, if detail records associated with an event are stored at an archiving database, the objective data associated with the event can include data retrieval information.

In addition to the various types of objective data that can be sensed, recorded or otherwise obtained at each field data source 100, subjective data can be provided by field data sources 100. More specifically, each data "package" associated with an event at one of field data sources 100 can include the local authorities' categorization of an event, an evaluation of the event, and the local response to the event. By way of illustrative example, the present invention will be described for use in monitoring/analyzing events that may be predictive or indicative of terrorist acts. Using this example, categorization data of an event is, in general, data that defines the likelihood that a particular event is related to an act of terrorism. For example, an event's category could be assigned a specific numeric or alphanumeric designation that subjectively defines the event as "normal" "non-suspicious", "suspicious", "highly suspicious", or "destructive". Another option is to utilize a sliding scale numeric category assignment. Thus, it is to be understood that the particular type of categorical designation is not a limitation of the present invention.

Evaluation of an event is the overall subjective evaluation of the event conducted by those directly in charge of the remote location supported by a field data source 100. Evaluations may be short or lengthy, and might describe a summary of the event and personal observations as to whether the event ended up being a false alarm, a real threat, a misunderstanding, an event ending in a fire fight, destruction of property or loss of life, etc. This data provides human interpretation of an event and can be a key element in establishing an ongoing database for associating objective data with subjective data and interpretation.

Data describing a local response to an event would include a description of what the field location did as a result of the event (e.g., immediately as the event was unfolding, and possibly just after the event). This data class could be used to establish a predictive base of causes, effects, and consequences.

Regardless of the systems/methods used by field data sources 100, all raw data "packages" produced in response to local events are provided (at step 200 in FIG. 2) to a field data collection and formatting subsystem 12. At subsystem 12, incoming raw data packages are collected and formatted in a consistent manner to facilitate processing by the remaining elements of system 10. While the particular format or template used to assemble the data into formatted data packages is not a limitation of the present invention, subsystem 12 typically separates the data into the following data classes:

date and time of an event;

system/method used to collect the data at the location where the event took place;

the type of location where the event took place such as an airport, border crossing, financial institution, utility, etc.;

the raw data record of the event such as image, video and/or audio recordings of the event;

identity data associated with individuals involved in the event such as names, social security numbers, passport numbers, biometric data, etc.;

category data that subjectively describes the likelihood that the event is of concern from the perspective of officials at the event;

evaluation data that subjectively evaluates the event from the perspective of officials at the event; and response data that subjectively describes how the event was handled by officials at the event.

Some or all of the above-described data classes will be supplied by each of field data sources 100.

Subsystem 12 could also be configured to append each formatted data package with additional data classes created by processing within system 10. For example, each formatted data package could reserve data classes for (i) an individual event assessment score (e.g., score assigned by system 10 designating the event as possibly being suspicious or critical), (ii) a correlation assessment score resulting from correlation of individual event data with other event data occurring concurrently at other locations, (iii) a "flag" value (e.g., a digital bit) set when events occur in particular countries, at particular sites/locations, or involve some predetermined materials or individuals, and (iv) recording the findings of system 10 associated with the event where the findings would have predictive value in associating and evaluating how system 10 handles/handled particular situations.

The formatted data packages are made available to a statistical processing block 14 where one or more statistical analyses of the formatted data packages is carried out (i.e., step 202 in FIG. 2), with the results thereof being stored in a database 16 (i.e., step 204 in FIG. 2). Each type of statistical analysis performed by statistical processing block 14 is carried out for events occurring in a number of unique time periods or blocks of time in step 202 (FIG. 2). For example, each statistical analysis could be performed by looking at all events reported by all field data sources 100 in the previous 1/5/10/30 minute blocks, 1/2/3/6/12/24 hour blocks, 1/2/5/7 day blocks, 2/3 week blocks, 1/2/3/6 month blocks, and 1/2/3/5/10 year blocks. The particular time periods or blocks used can be more, less, or different than these without departing from the scope of the present invention. Each statistical analysis relates the event data from the most recent of the time blocks to historical ones of the same time blocks. By confining each statistical analysis to the same time block, coordinated events may be detectable as patterns or as high correlations as will be described further below. Since time may be of the essence, it is preferred that the statistical analyses for the various time blocks be carried out concurrently using parallel processors or parallel processing techniques.

The number and type of statistical analyses can be many and varied. By way of example, several types of statistical analyses will be described briefly herein. One type of statistical analysis is a summary statistics generator that calculates continuous statistics on all incoming data. In particular, it would calculate and record total number of reported events in the most recent time blocks (specified by processing 14) in each event category and for each reporting location. As will be described further below, system 10 uses these summary statistics to determine if there are inconsistencies between instantaneous and historical measures of activity. As time evolves and database 16 accrues large amounts of historical data, instantaneous summary statistics can be compared with statistics associated with known previous dangerous and high terrorist activity periods.

Another type of statistical analysis could calculate and record total number of reported events with similar biometric indicators in the most recent time blocks in each event category and for each reporting location. System 10 uses these statistics to compare historical data with instantaneous data to determine if there are inconsistencies between instantaneous and historical measures of activity. With the biometric data, there is also a great degree of individual identity information specificity. Consequently, system 10 could further access underlying identification information to establish potential problems based on pre-established association of identified individuals with other individuals involved in past reported events.

Still another type of statistical analysis examines the objective record data from an event such as movement data (e.g., speed of movement, use of certain vehicles or means of transportation, airlines losing contact with FAA tracking system, high rate of closure of trucks with sentry gates, etc.). Here, statistical processing 14 calculates and records on a continuous basis the total number of reported events with similar activity indicators in the most recent time blocks in each event category and in each reporting location. The interest here is in anticipating individual terrorist events, as well as determining if coordinated synchronized attacks on multiple locations are in process.

On a continuous basis, statistical processing 14 could also be used to calculate and record the total number of reported events with similar pattern indicators in the most recent time blocks in each event category and for each reporting location. This statistical analysis would examine all the data classes together for overall patterns and deviations from "running averages" or historical patterns. Such pattern analysis is well established in a variety of fields and any well known technique of pattern analysis could be used here (e.g. regression tree classification, artificial neural networks, principal component analysis, etc.).

A correlation processing block 18 uses the results stored in database 16 to perform a number of correlations at step 206. In general, the correlations compare the various time block-based results. For example, one correlation might compare results from all events across the most recently occurring time blocks. Patterns occurring across data classes from a variety of events could be identified by such correlations. Another type of correlation could compare the results form the most recent time blocks with results from historic ones of the same time blocks to see how the most recent time block-based results are correlated with historic ones of the same time blocks. Since the results and response from the historic events are known, this type of correlation provides predictions of consequences and possible responses to the most recent event. A high correlation can be indicated when a correlation score exceeds a predetermined threshold (developed using historic events) associated with a data class. Correlation processing 18 could also be used to search for the occurrence of particular types/values of category data associated with an event (e.g., indicative of "highly suspicious" or "destructive" events). As with the statistical processing, it is preferred that the various types of correlation processing are carried out using parallel processors and parallel processing techniques.

The patterns, correlation scores and/or specific category-type data events identified by correlation processing 18 can be provided to an alert generation system 20 (i.e., step 208 in FIG. 2) which can be an automated system. Thus, event monitoring and analyzing system 10 uses event statistics and correlation processing that "ingests" event data from multiple events occurring at geographically-dispersed locations. If a remote field-site event report indicates a terrorist event is underway or a highly suspicious event is underway, an emergency alert may be issued to all sites connected to system 10. This automated alert would allow systems and individuals to increase readiness. Concurrently, system 10 (i) analyzes record, biometric, activity, and pattern data associated with the current event to identify the event as being indicative of future terrorist or highly suspicious events, and (ii) evaluates incoming data from other locations to determine if similar events are underway at other locations.

Other additional concurrent correlation processes could include (i) comparing current event data coming in from the field to historically known event data patterns with known destructive consequences, and (ii) continuous event analysis over all regions or specific geographic regions as well as category oriented analysis (e.g., are there a number of remote sites in a given category reporting events, are there several ships transmitting unusual event data at the same or proximate times, are there a number of embassies transmitting unusual event data at the same time, etc.).

The results of individual analyses and statistical summaries are compared to thresholds and historical statistics by the correlation processing of the present invention. If either the statistics exceed thresholds or if multiple events seem to be coming at higher than normal rates in short time intervals, a coordinated attack may be underway for which an appropriate level of alert would be generated. All processed results are archived and can be appended to individual event data files when appropriate.

The present invention can also be used in other modes. For example, a subsystem that handles external queries could be added to system 10. With this subsystem, an analyst at some security, defense, or intelligence agency would be able to query the system for information on a particular pattern of events or for information on events occurring during a particular time interval, or for a particular location.

Since the present invention will require and maintain large and growing databases, a continuous background process could be used to refine thresholds and utilize standard data mining techniques for generating new candidate criteria for alert generation. Finally, the system could also maintain running statistics of event reporting for each remote site. If the level of interaction or event reporting from a particular site falls below some threshold, this might indicate problems or emergencies at the remote site. Accordingly, failure to receive any event reports from field data sources during predefined times (which would be the case if a remote site was destroyed or incapacitated), would itself be a trigger for an alert to be issued.

Thus, although the invention has been described relative to a specific embodiment thereof, there are numerous varia-

What is claimed as new and desired to be secured by Letters Patent of the United States is:

1. A method of monitoring and analyzing event data associated with activities of concern, said method comprising the steps of:
    collecting raw data packages from a plurality of locations dispersed over a large geographic area, each raw data package originating at a location, each raw data package including data selected from the group of data classes consisting of:
    (i) date and time of an event,
    (ii) means used to collect said data at said location,
    (iii) a record of said event;
    (iv) type of said location where said event occurred,
    (v) identification data collected at said event and associated with individuals involved in said event,
    (vi) a category assigned to said event at said location,
    (vii) an evaluation of said event that originates at said location, and
    (viii) a response to said event implemented at said location;
    performing a plurality of statistical analyses concurrently for each of said plurality of unique time periods using each of said raw data packages wherein statistical results of said statistical analyses are generated, each of said plurality of statistical analyses being based on one of a plurality of unique time periods wherein each of said plurality of statistical analyses relates ones of said raw data packages occurring in a most recent one of said plurality of unique time periods to ones of said raw data packages occurring in historical ones of said plurality of unique time periods;
    storing said statistical results in a database;
    performing a plurality of correlations using said results to generate correlation results; and
    sending an alert to at least a portion of said plurality of locations based on said correlation results.

2. A system for monitoring and analyzing event data associated with activities of concern, said system comprising:
    means for collecting raw data packages from a plurality of locations dispersed over a large geographic area, each raw data package originating at a location, each raw data package including data selected from the group of data classes consisting of:
    (i) date and time of an event,
    (ii) means used to collect said data at said location,
    (iii) a record of said event;
    (iv) type of said location where said event occurred,
    (v) identification data collected at said event and associated with individuals involved in said event,
    (vi) a category assigned to said event at said location,
    (vii) an evaluation of said event that originates at said location, and
    (viii) a response to said event implemented at said location;
    means for arranging said data from each of said raw data packages into a standardized template indexed by said data classes;
    at least one statistical processor for performing a plurality of statistical analyses using each of said raw data packages arranged in said standardized template wherein statistical results of said statistical analyses are generated, each of said plurality of statistical analyses being based on one of a plurality of unique time periods wherein each of said plurality of statistical analyses relates ones of said raw data packages occurring in a most recent one of said plurality of unique time periods to ones of said raw data packages occurring in historical ones of said plurality of unique time periods;
    a database coupled to said at least one statistical processor for storing said statistical results;
    at least one correlation processor coupled to said database for performing a plurality of correlations using said statistical results wherein correlation results are generated; and
    an alert generating system coupled to said at least one correlation processor for sending an alert to at least a portion of the locations based on said correlation results.

3. A system as in claim 2 wherein said at least one statistical processor utilizes parallel processing to perform said plurality of statistical analyses concurrently for each of said plurality of unique time periods.

4. A system as in claim 2 wherein said at least one correlation processor utilizes parallel processing to perform said plurality of correlations concurrently.

5. A system as in claim 2 wherein said plurality of unique time periods range in duration from approximately 1 minute to a plurality of years.

6. A system as in claim 2 wherein said activities of concern comprise acts of terrorism, and wherein said category assigned to said event defines a likelihood that said event is associated with an act of terrorism.

7. A system as in claim 2 wherein said identification data comprises biometric data collected from said individuals involved in said event.

8. A system as in claim 2 wherein said record of said event comprises at least one of visible images of said event and audible recordings of said event.

* * * * *